United States Patent [19]

Hour

[11] Patent Number: 4,805,648

[45] Date of Patent: Feb. 21, 1989

[54] AUTOMATIC WASHING AND STERILIZING DEVICE FOR A STABLE

[76] Inventor: Tyh-Yuan Hour, 82, To-Syh Village, Luh-Jeau Shian, Chiayi Hsien, Taiwan

[21] Appl. No.: 129,168

[22] Filed: Dec. 7, 1987

[51] Int. Cl.$^4$ .............................................. B08B 3/00
[52] U.S. Cl. ..................................... 134/57 R; 134/98; 134/100; 134/123; 134/178; 212/210; 239/243; 239/752
[58] Field of Search .................... 134/57 R, 172, 173, 134/98–100, 123, 178, 210; 239/750, 751, 752, 753, 243, 263.1, 263.2, 263.3, 264; 212/207, 76, 118

[56] References Cited

U.S. PATENT DOCUMENTS

| | | | |
|---|---|---|---|
| 815,963 | 3/1906 | Locher | 212/118 X |
| 3,107,676 | 10/1963 | Thorson et al. | 134/178 X |
| 3,391,701 | 7/1968 | Richardson et al. | 239/243 X |
| 3,908,907 | 9/1975 | Beltran | 239/752 |
| 3,985,161 | 10/1976 | Nelson | 239/751 |

Primary Examiner—Harvey C. Hornsby
Assistant Examiner—Stephen F. Gerrity
Attorney, Agent, or Firm—Larson and Taylor

[57] ABSTRACT

An automatic washing and sterilizing apparatus for a stable provided with shooting and spraying nozzles fixed on two cranes which can be moved right and left in the stable by means of two wires wound around wire drive wheels driven by a speed transmission system connected with motors. The nozzles are connected with pipes and valves to shoot or spray water or sterilizing solution selectively. The moving direction of the cranes is altered by two locating switches having a control bar to be touched by the plates of the cranes.

5 Claims, 6 Drawing Sheets

FIG. 1

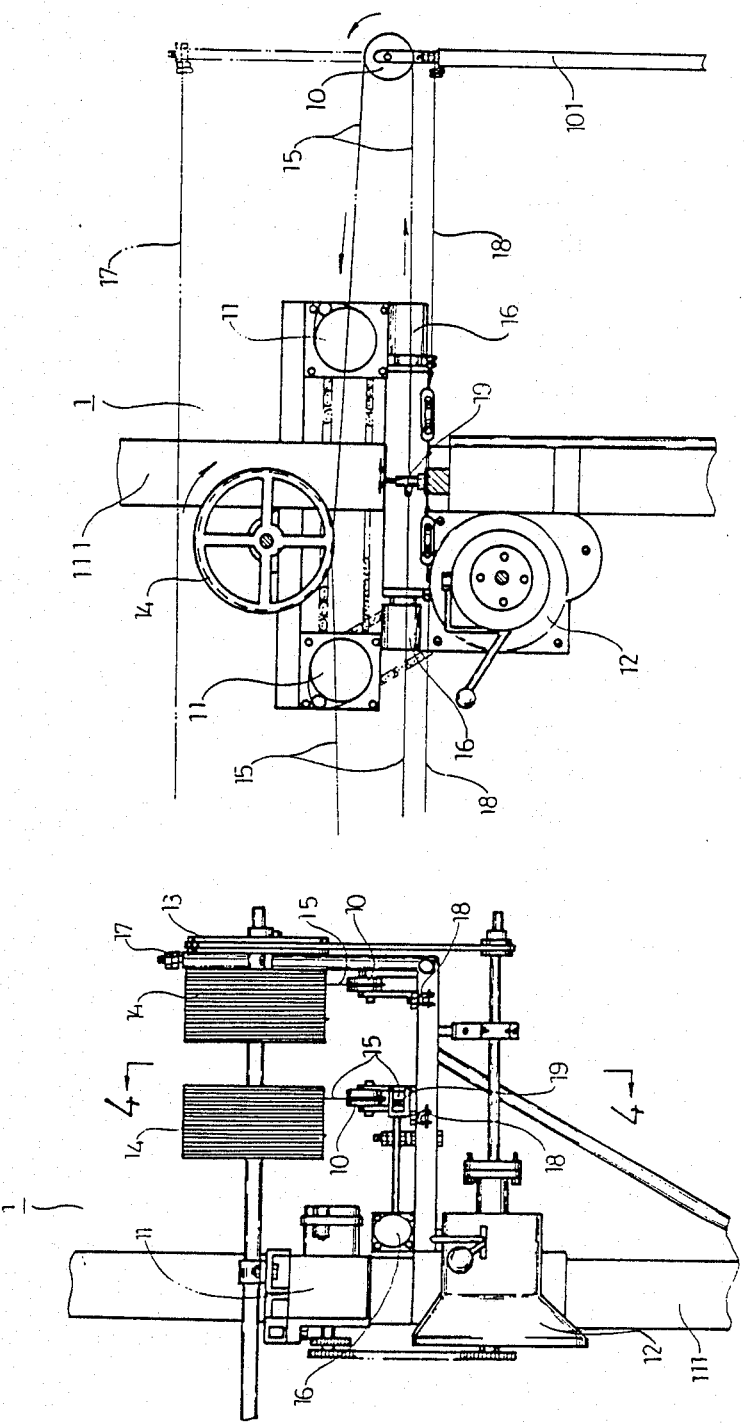

AUTOMATIC WASHING AND STERILIZING DEVICE FOR A STABLE

BACKGROUND OF THE INVENTION

Traditional stables for feeding pigs, cows, etc. are generally washed often and sterilized at a regular interval, but these operations are done by workers with hoses and spray guns so it requires a large expenditure in a big-scaled stable.

SUMMARY OF THE INVENTION

In view of the importance of the sanitary and sterilizing job to a stable, the inventor has provided an automatic washing and sterilizing device in order to save the manual work and the workers' wage.

This device includes shooting and spraying nozzles which can shoot or spray water or sterilizing solution supplied by a pump through pipes and valves. The nozzles are fixed on two cranes, each crane hanging from a wire rope, sometimes referred to simply as a "wire", and pulled to move in one or the other direction by a wire rope which is pulled by a wire drive wheel about which the wire is wound. The shaft of the wire drive wheels is the same shaft onto which a fly wheel is fixed to be rotated by a speed transmission connected with two motors. The alteration of the moving direction of the cranes is accomplished by a control bar which cooperates with locating switches when one of the cranes comes to touch said control bar.

BRIEF DESCRIPTION OF THE DRAWINGS

FIG. 1 is an plan view of the device of the present invention.

FIG. 3 is a left side view of the device of the present invention.

FIG. 4 is a cross-sectional view taken along line 4—4 on FIG. 3.

DETAILED DESCRIPTION OF THE INVENTION

Figure 1:
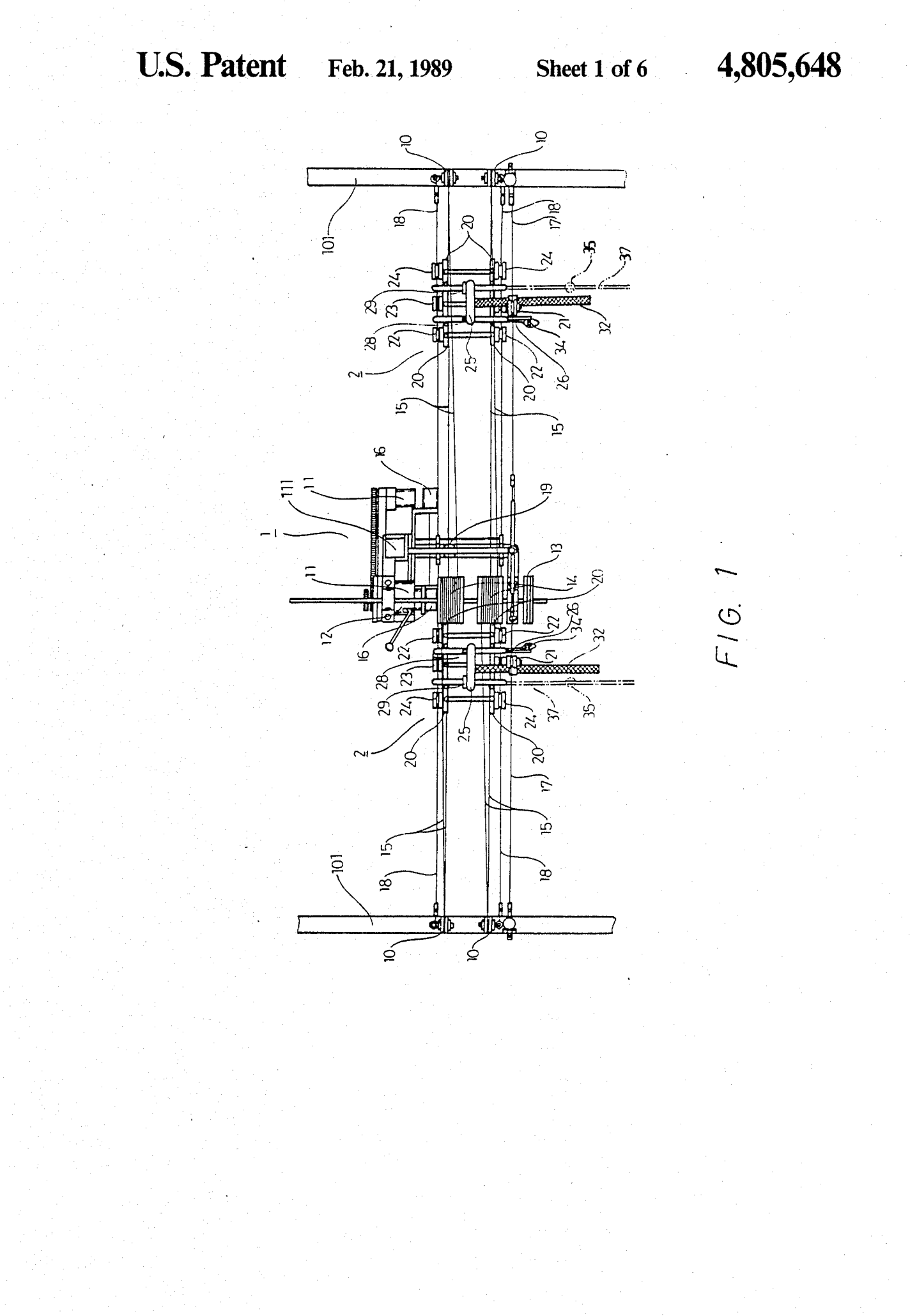
Figure 2:
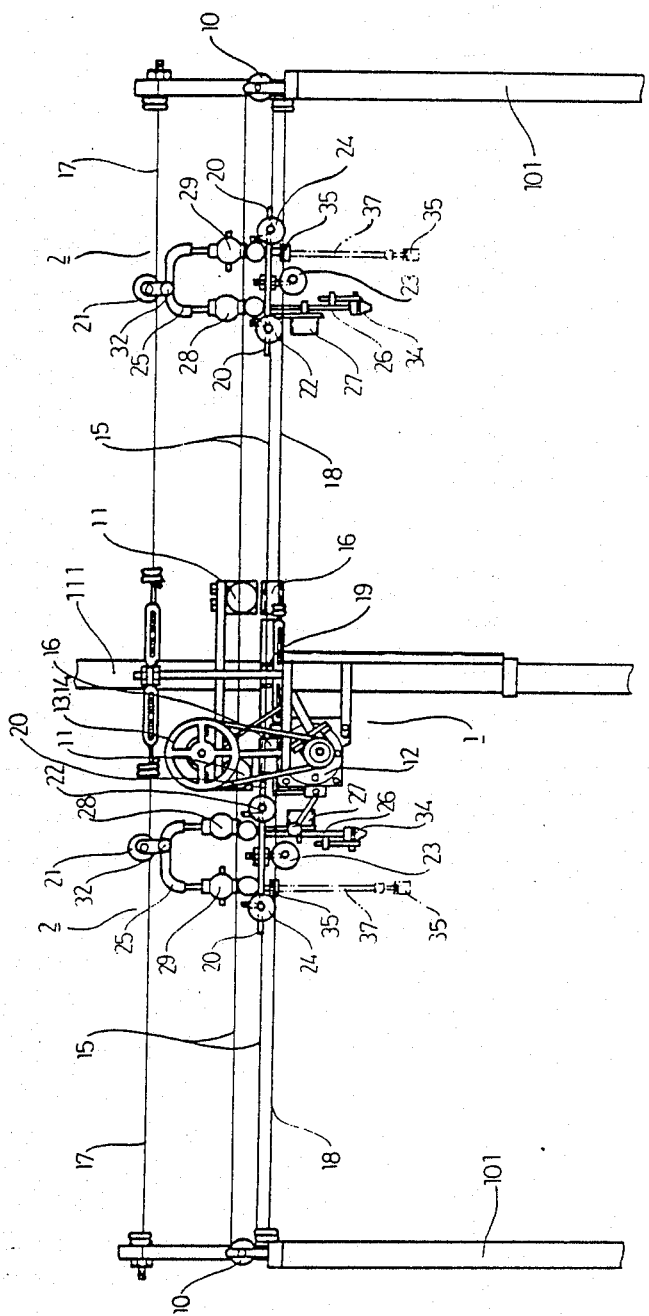
FIG. 2 is a front view of the device of the present invention.

This automatic washing and sterilizing device for a stable shown in FIGS. 1, 2 and 3 includes main transmission system 1 which comprises two motors 11 combined with speed transmission 12 to drive fly wheel 13. Two wire drive wheels 14 fixed on the same shaft as that of fly wheel 13 are and rotated to pull two cranes 2 to move synchronously by means of wire ropes 15 wound around wire drive wheels 14. Both ends of wire ropes 15 are fixed at both ends of a plate 20 which is combined with two groups of pulleys 22, 23 and 24.

Two cranes 2 are located separately at each side of two locating switches 16 located near the central post 111, to be pulled to move by wire ropes 15 wound around wire drive wheels 14. Cranes 2 move right and left hanging from fixed wire ropes 17 set at a higher level and fixed wire ropes 18 set at a lower level. When one of the cranes 2 comes to touch control bar 19 united with locating switches 16, said switches activate to cause motors 11 to turn in the opposite direction to make wire drive wheels 14 also rotate in the opposite direction as motors 11 so that cranes 2 may move in the opposite direction.

Main transmission system 1 shown in FIGS. 3 and 4 is installed on the central post 14 of the stable and includes two guiding wheels 10 which are mounted on end posts 101. The wheels 10 guide wire ropes 15 as they alter their moving direction.

One of motors 11 turns in one direction and the other in the opposite direction and both are separately controlled to change the turning direction by locating switches 16 which work according to the change of control bar 19 set at the center between the two cranes 2. Control bar 19 activates locating switches 16 when it is touched by plates 20 of either of said cranes 2.

Figure 5:
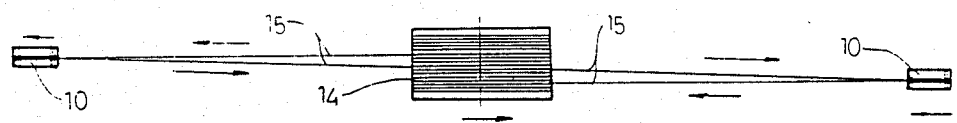
FIG. 5 is an plan view of the wire rope wound around the wire wheel of the present invention.
Figure 6:
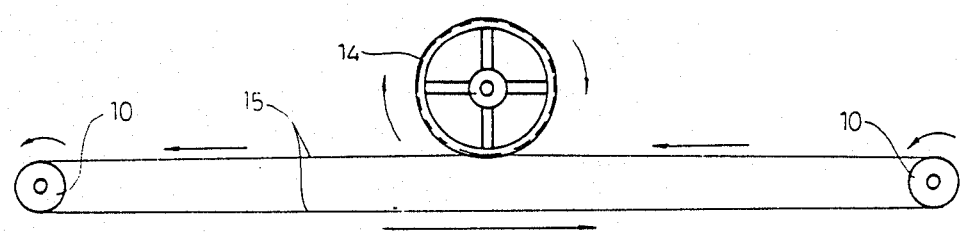
FIG. 6 is a front view of the wire rope wound around the wire wheel of the present invention.

Wire ropes 15 shown in FIGS. 5 and 6 wind around wire drive wheels 14 at the center and guiding wheels 10 at both ends, and the rotation of wire drive wheels 14 can cause wire ropes 15 to move around continously. Both ends of each wire rope 15 are fixed at both ends of a plate 20 fixed on each crane 2.

Figures 7, 8:
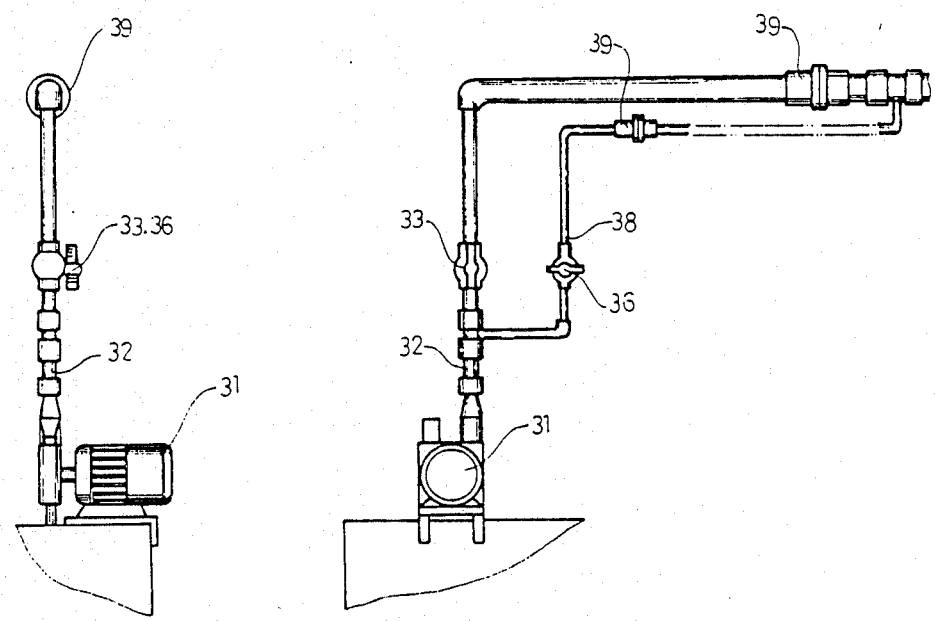
FIG. 7 is a front view of the liquid transporting system of the present invention.
FIG. 8 is a side view of the liquid transporting system of the present invention.
Figure 10:
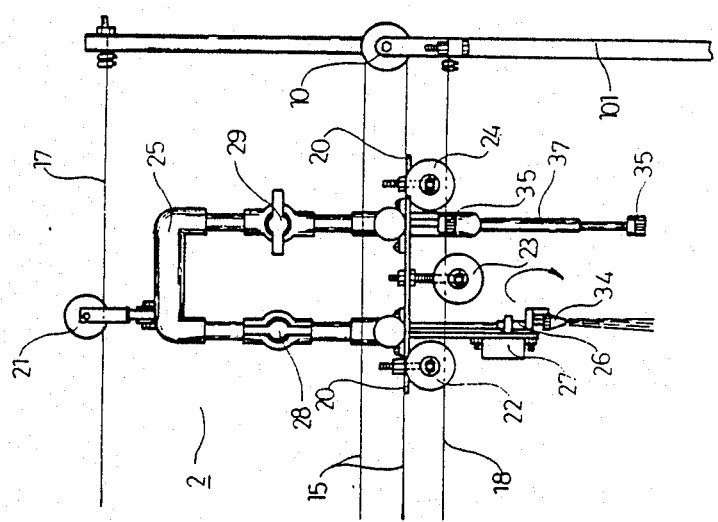
FIG. 10 is a front view of the crane of the present invention.
Figure 9:
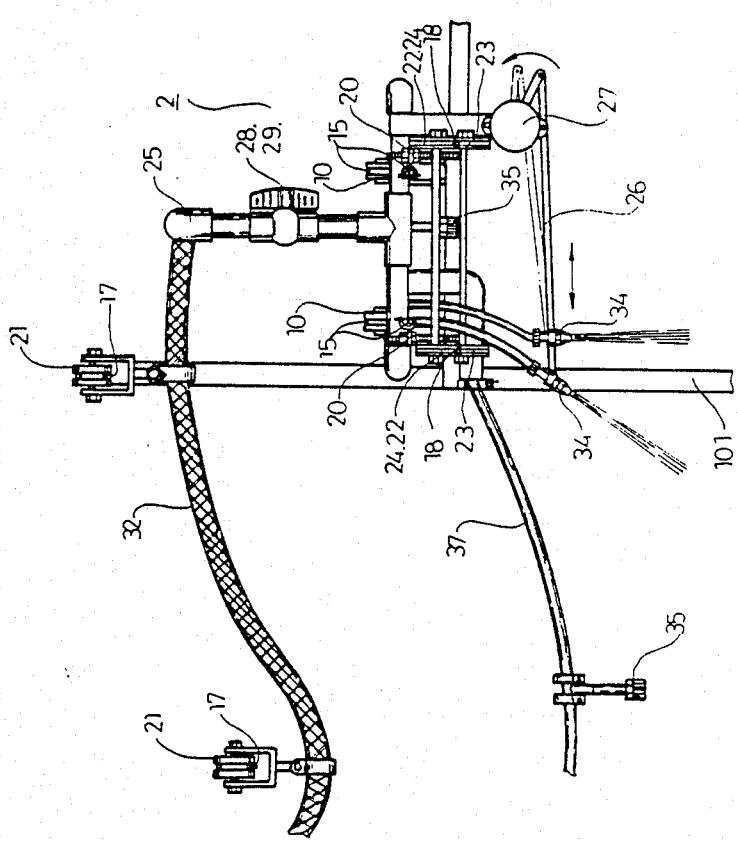
FIG. 9 is a side view of the crane of the present invention.

A powerful pump 31 comprised in the liquid shooting and spraying system shown in FIGS. 7 and 8 sucks up the water from a tank or a pond into water pipe 32 through valve 33 and to nozzles 34 shown in FIGS. 9 and 10, which can shoot out the water. Also, at one side of water pipe 32 is set solution tube 38 for transporting sterilizing solution to nozzles 35 through valve 36 opened and also through water pipe 32. In addition, check valve 39 is fixed separately on water pipe 32 and on solution tube 38 to prevent the back flow.

Figure 12:
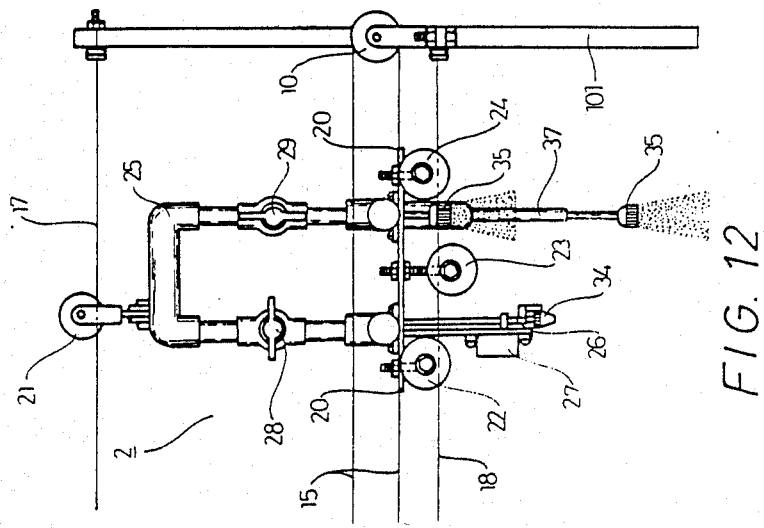
FIG. 12 is another front view of the crane of the present invention.
Figure 11:
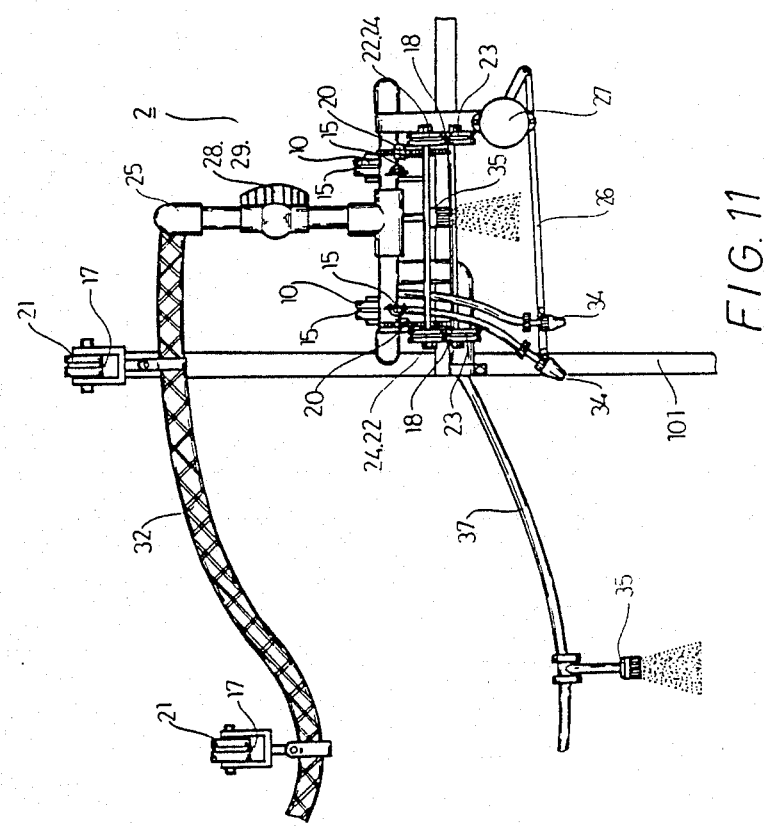
FIG. 11 is another side view of the crane of the present invention.

Next, each crane 2 includes pulley 21 for hanging on wire rope 17 set between both end posts 101 and the central post 111, two groups of three pulleys 22, 23, and 24 fixed on plates 20 pinching wire rope 18 and located symmetrically at the front and the rear of the each crane. The cranes move steadily right and left hanging from wire ropes 17 and 18, and three pulleys 22, 23 and 24 can be adjusted higher or lower to keep a proper tightness for pinching wire rope 18 between them. Also, cranes 2 are constructed for fixing nozzles for shooting out or spraying liquid, including pulleys 21-24 running along wire ropes 17 and 18 and metal or hard plastic pipe 25 connected with valves 28 and 29 for choosing water or sterilizing solution to be shot out through nozzles 34 or to be sprayed out through nozzles 35, as shown in FIGS. 11 and 12.

Nozzles 34 are connected with linking rod 26 and moved slowly by synchronous motors 27 in order to cover a wide area of washing in the stable, and nozzles 35 are connected with soft tubes 37 and also moved slowly by said cranes 2 to cover a wide area of spraying.

In general, this automatic washing and sterilizing device can automatically make a regular job of washing and sterilizing selectively with water or with sterilizing solution in a shooting or a spraying way.

What is claimed is:

1. An automatic washing and sterilizing apparatus for washing and sterilizing a space located beneath the apparatus, such as a stable or the like, comprising:

frame means for mounting wires so as to extend over the space, a set of fixed wires extending across the space and secured by said frame means, and a set of moving wires mounted on pulleys secured to the frame means, a main transmission system fixed above the space in the vicinity of the wires and intermediate between said frame means, said transmission system including a pair of motors, each operable in a different direction, and a plurality of wire drive wheels, each wire drive wheel being encircled by a moving wire such that turning of the wire drive wheels moves the wires lengthwise between said frame means, turning about said pulleys, said wire drive wheels operatively connected to the motors to be operated thereby, said main transmission system including a control means which, when engaged in one direction operates one of the two motors and when engaged in the other direction operates the other motor, a pair of cranes mounted on the fixed and movable wires, one crane on each side of the main transmission system, each crane supported by the fixed wires for movement therealong and fixedly securable to the movable wires for movement therewith, such that as the wire drive wheels move the moveable wires and hence both cranes in one direction, both cranes move synchronously, one crane moving toward the main transmission system and the other moving away from the main transmission system toward the frame means on that side, and wherein when the wire drive wheels move in the other direction, both cranes move synchronously in that other direction, each crane having a stop means positioned to engage the control means of the main transmission system as that crane reaches the main transmission system, to cause the control means to turn off one motor and turn on the other motor, to thereby reverse the direction of movement of the wire drive wheels, the moveable wires and hence also the two cranes, and a liquid shooting and spraying system including nozzles fixed onto the cranes for movement therewith as the cranes move with the moveable wires, said nozzles being directed downwardly to shoot and spray liquid into the space located therebelow, a liquid supply means including a pump and flexible hoses for delivering liquid to the nozzles at the cranes.

2. An apparatus according to claim 1, each said crane comprising a plate having a plurality of pulleys which pinch the moveable wires to secure the plates thereto so that the plates and their respective cranes can move therewith, each said plate comprising the stop means which engages the control means of the main transmission system as that crane reaches the main transmission system.

3. An apparatus according to claim 2, wherein the pulleys on the plates are adjustable to adjust the tightness with which they pinch the moveable wires.

4. An apparatus according to claim 3, including two groups of three pulleys on each plate, each group engaging a different moveable wire.

5. An apparatus according to claim 1, including a pair of wire drive wheels, each engaging a different moveable wire which is wound therearound and frictionally engaged therewith, such that turning of a wire drive wheel moves its respective moveable wire.

* * * * *